US008658390B2

(12) United States Patent
Urade et al.

(10) Patent No.: US 8,658,390 B2
(45) Date of Patent: Feb. 25, 2014

(54) METHOD FOR DETECTING MUSCLE DEGENERATIVE DISEASES, AND METHOD FOR DETERMINING THERAPEUTIC EFFICACY ON THE DISEASES

(75) Inventors: Yoshihiro Urade, Suita (JP); Kosuke Aritake, Suita (JP); Toshihiko Maruyama, Suita (JP); Shinya Kamauchi, Suita (JP); Shin'ichi Takeda, Kodaira (JP); Akinori Nakamura, Kodaira (JP)

(73) Assignees: Osaka Bioscience Institute, Suita-shi, Osaka (JP); National Center of Neurology and Psychiatry, Kodaira-shi, Tokyo (JP); Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/255,120

(22) PCT Filed: Mar. 8, 2010

(86) PCT No.: PCT/JP2010/053762
§ 371 (c)(1),
(2), (4) Date: Sep. 7, 2011

(87) PCT Pub. No.: WO2010/104025
PCT Pub. Date: Sep. 16, 2010

(65) Prior Publication Data
US 2011/0318764 A1    Dec. 29, 2011

(30) Foreign Application Priority Data
Mar. 9, 2009   (JP) ................................ 2009-055057

(51) Int. Cl.
*G01N 33/53*    (2006.01)
(52) U.S. Cl.
USPC ........................................................ 435/7.92
(58) Field of Classification Search
None
See application file for complete search history.

(56) References Cited

U.S. PATENT DOCUMENTS

| 7,238,718 | B2 | 7/2007 | Urade et al. | |
| 2009/0281098 | A1 | 11/2009 | Urade et al. | |
| 2010/0209962 | A1* | 8/2010 | FitzGerald et al. | ............. 435/29 |

FOREIGN PATENT DOCUMENTS

| EP | 1911755 A1 | 4/2008 |
| JP | 2005-119984 A | 5/2005 |
| JP | 2010-02416 A | 1/2010 |
| WO | 2009043015 A1 | 4/2009 |

OTHER PUBLICATIONS

Takeshi Okinaga et al., "Induction of hematopoietic prostaglandin D synthase in hyalinated necrotic muscle fibers: its implication in grouped necrosis", Acta Neuropathol, 2002, vol. 104, No. 4, p. 377-384 Abstract.

Wen-Liang Song et al., "Tetranor PGDM, an Abundant Urinary Metabolite Reflects Biosynthesis of Prostaglandin D2 in Mice and Humans", J Biol Chem, Jan. 11, 2008, vol. 283, No. 2, p. 1179-1188 Abstract, Figure 1.

Cathy K. Ellis et al., "Metabolism of Prostaglandin D2 in the Monkey", J Biol Chem, 1979, vol. 254, No. 10, p. 4152-4163; fig. 20 XIII, p. 4162, right column, lines 3 to 5.

Ikuko Mohri et al., "Inhibition of Prostaglandin D Synthase Suppresses Muscular Necrosis", Am J Pathol, May 2009, vol. 174, No. 5, p. 1735-1744; entire text.

Shinya Kamauchi et al., "Dobutu Model ni Okeru Prostaglandin D2 Nyouchu Taishabutsu no Hendo", Journal of Japanese Biochemical Society, Sep. 25, 2009, abstract CD Page.ROMBUN No. 2P-138; entire text.

M Kondo et al., 15-Deoxy-[Delta]<12, 14>-prostaglandin J2: The endogenous electrophile that induces neuronal apoptosis, Proceedings of the National Academy of Sciences of the United States of America, vol. 99, No. 11, May 28, 2002, p. 7367-7372.

* cited by examiner

*Primary Examiner* — John Ulm
(74) *Attorney, Agent, or Firm* — Rothwell, Figg, Ernst & Manbeck, P.C.

(57) ABSTRACT

Muscle degenerative diseases can be detected in the early stage and the therapeutic efficacy of a therapeutic agent and/or a therapy method for the diseases can be determined by measuring 11,15-dioxo-9α-hydroxy-2,3,4,5-tetranorprostan-1,20-dioic acid (referred to as "Tetranor-PGDM", hereinbelow) in a sample isolated from a subject.

4 Claims, 1 Drawing Sheet

METHOD FOR DETECTING MUSCLE DEGENERATIVE DISEASES, AND METHOD FOR DETERMINING THERAPEUTIC EFFICACY ON THE DISEASES

CROSS REFERENCE TO RELATED APPLICATION

This application is a 35 U.S.C. 371 National Phase Entry Application from PCT/JP2010/053762, filed Mar. 8, 2010, which claims the benefit of Japanese Patent Application No. 2009-055057 filed on Mar. 9, 2009, the disclosure of which is incorporated herein in its entirety by reference.

TECHNICAL FIELD

The present invention relates to a method for early detection of muscle degenerative diseases, and a method for predicting and/or determining a therapeutic agent and/or a therapeutic method.

BACKGROUND ART

Groups of diseases involving muscular disorder or myonecrosis are called myopathy. Muscular dystrophy and amyotrophy are representative examples of this class of disease. Muscular dystrophy is a collective term used for hereditary diseases that are characterized by gradual muscle weakening and atrophy. Progressive muscular dystrophies affect the largest number of patients, and cause hereditary, progressive muscle weakness. Amyotrophy is a neurogenic disease caused by damages in motor nerve.

The type of muscular dystrophy that affects the largest number of patients is Duchenne muscular dystrophy, which is a sex-linked recessive hereditary disease that develops only in males. The disease affects 3 to 5 individuals per 100,000 people, and 1 in 2,000 to 3,000 newborn males. The disease generally develops at the age of about 3 to 5 with defects in walking and standing, such as running problems and frequent falls. The ability to walk is lost by the age of around 10. These symptoms are followed by a rapid progress of spinal column deformation and arthrogryposis, which in many cases lead to respiratory failure, and, less often, heart failure and pneumonia.

The tests used for the diagnosis of muscular dystrophy include a blood test, a nerve conduction test, electromyography, a muscle biopsy, and a DNA analysis. The nerve conduction test finds whether mobility impairment or perception impairment stems from peripheral neuropathy, or looks for a damaged site or the extent of damage. The test measures the conduction rate of a stimulus in an electrostimulated nerve. By nature, the test requires special equipment, and, because an electrostimulation is directly applied to the nerve, the test is somewhat demanding in the sense that it involves shock, pain, and discomfort.

Electromyography finds whether mobility impairment originates in muscle or nerve, or looks for a damaged site or the extent of damage. The test requires special equipment, and involves pain from the insertion of a needle into the muscle. Pain-free, surface electromyography is available; however, the measurement must be performed at test facilities.

Muscle biopsy requires collecting a muscle tissue, and is therefore invasive and inconvenient. DNA analysis, necessary for the diagnosis of Duchenne and Becker muscular dystrophies caused by a mutation in the dystrophin gene, has not been applied to muscle degenerative diseases, and lacks versatility.

The blood test generally looks for creatine kinase. Creatine kinase is an enzyme predominantly present in the soluble fractions of skeletal muscle and cardiac muscle, and leaks into the blood from damaged cells. A damaged or dead skeletal muscle considerably raises the blood creatine kinase levels, and such high levels of blood creatine kinase can thus be used for the diagnosis of muscular dystrophy. However, because the blood creatine kinase levels can also increase in other diseases, a differential diagnosis solely based on creatine kinase concentration is difficult, and is made simultaneously with other tests.

The blood test that measures the blood creatine kinase is also performed for other progressive muscular dystrophies, and for diseases that involve muscle damage or death caused by nerve defects. However, as above, high blood creatine kinase levels also occur in diseases other than muscular disorders and myonecrosis, and other markers for muscular disorders and myonecrosis are needed.

Accordingly, there is a need for a method or a diagnosis kit that enables an early and easy diagnosis of muscle degenerative diseases such as muscular dystrophy.

11,15-Dioxo-9α-hydroxy-2,3,4,5-tetranorprostan-1,20-dioic acid (hereinafter, Tetranor-PGDM) is known as a metabolite of prostaglandin $D_2$ (hereinafter, $PGD_2$), and there is a report that the Tetranor-PGDM excreted into the urine increases through inflammation reactions in humans and mice, and that Tetranor-PGDM is a marker that reflects $PGD_2$ production (Non-Patent Literature 1).

There are also reports that the increased expression of hematopoietic prostaglandin D synthetase (hereinafter, HPGDS) that catalyzes $PGD_2$ production occurs at the affected sites of muscle degenerative diseases such as muscular dystrophy, and that $PGD_2$ is involved in the prevention and improvement of disease progression (Patent Literature 1, Non-Patent Literature 2).

It is not known, however, that Tetranor-PGDM is detected in high concentrations as an excretion in the urine of patients with muscle degenerative diseases, and that the Tetranor-PGDM concentration significantly decreases by the administration of an HPGDS inhibitor.

CITATION LIST

Patent Literature

PTL 1: Japanese Unexamined Patent Publication No. 2005-119984

Non-Patent Literature

NPL 1: J. Biol. Chem., Vol. 283, No. 2, 1179-1188 (2008)
NPL 2: Acta Neuropathol, 104, 377-384 (2002)

SUMMARY OF INVENTION

Technical Problem

It is an object of the present invention to provide a method for efficient diagnosis of a muscle degenerative disease through the measurement of urine Tetranor-PGDM, and a method for determining the therapeutic efficacy of a therapeutic agent and/or a therapeutic method for such diseases.

Another object of the present invention is to provide a muscle degenerative disease diagnosis kit that targets Tetranor-PGDM.

Solution to Problem

The present inventors conducted intensive studies to achieve the foregoing objects, and completed the invention based on the following findings.
1) A muscular dystrophy model animal had elevated levels of the $PGD_2$ metabolite Tetranor-PGDM in urine compared to normal animals.
2) The administration of a known $PGD_2$ synthetase inhibitor to a muscular dystrophy model animal lowered the amount of Tetranor-PGDM excreted into the urine.

The present invention provides a method for detecting a muscle degenerative disease, a kit for the diagnostic measurement of a muscle degenerative disease, and a kit for predicting and/or determining the efficacy of a therapeutic agent and/or a therapeutic method for muscle degenerative diseases, as follows.

Item 1.
A method for detecting a muscle degenerative disease, the method comprising the step of measuring a Tetranor-PGDM content in a sample isolated from a subject.

Item 2.
A method for determining the efficacy of a therapeutic agent and/or a therapeutic method for a muscle degenerative disease, the method comprising the step of measuring a Tetranor-PGDM content in a sample isolated from a muscle degenerative disease patient.

Item 3.
The method according to Item 1 or 2, wherein the sample is urine.

Item 4.
The method according to any one of Items 1 to 3, wherein the Tetranor-PGDM is measured by using high-performance liquid chromatography-tandem mass spectrometry (HPLC-MS/MS), enzyme immunoassay (EIA), radioimmunoassay (RIA), fluorescent immunoassay (FIA), ELISA, or an enzymatic method.

Item 5.
The method according to Item 1 or 2, wherein the muscle degenerative disease is progressive muscular dystrophy, congenital muscular dystrophy, limb-girdle muscular dystrophy, facioscapulohumeral muscular dystrophy, myotonic muscular dystrophy, amyotrophic lateral sclerosis, or myopathy.

Item 6.
A diagnosis measurement kit for a muscle degenerative disease, the kit comprising an antibody against Tetranor-PGDM.

Item 7.
A kit for predicting and/or determining the efficacy of a therapeutic agent and/or a therapeutic method for a muscle degenerative disease, the kit comprising an antibody against Tetranor-PGDM.

Item 8.
The kit according to Item 6 or 7, comprising the antibodies against Tetranor-PGDM, labeled Tetranor-PGDM, and, optionally, at least one selected from the group consisting of an anti-immunoglobulin antibody, a sample diluting solution, a diluting solution for the antibody and the labeled Tetranor-PGDM, standard Tetranor-PGDM of a known concentration, an EIA substrate, and an EIA stop solution.

Advantageous Effects of Invention

The present invention enables an easy and early diagnosis of a muscle degenerative disease through the measurement of Tetranor-PGDM in a sample isolated from a subject, and can effectively determine the therapeutic efficacy of a therapeutic agent and/or a therapeutic method for such diseases.

The present invention also can be used as a diagnosis kit for an easy diagnosis of muscle degenerative diseases, by using increased urine Tetranor-PGDM as a marker.

DESCRIPTION OF EMBODIMENTS

Figure 1:
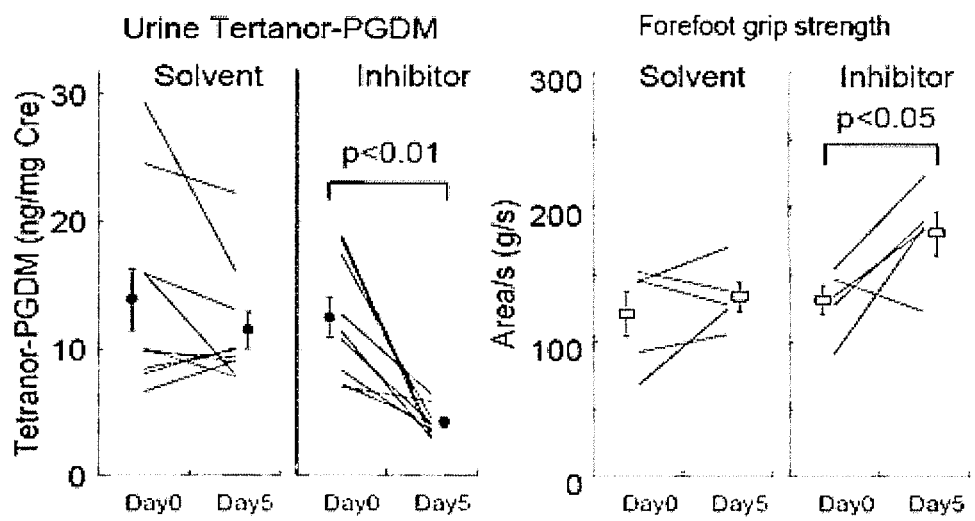
FIG. 1 is a diagram showing changes in urine Tetranor-PGDM concentration and forefoot grip strength in mdx mice administered with an HPGDS inhibitor.

The present invention enables the diagnosis of muscle degenerative diseases using Tetranor-PGDM as an index, and can effectively determine the therapeutic efficacy of therapeutic agents and/or therapeutic methods for these diseases. Further, by using Tetranor-PGDM as a marker, the invention can provide a diagnosis kit for these diseases, or a kit for predicting and/or determining the efficacy of therapeutic agents and/or therapeutic methods for muscle degenerative diseases.

According to an embodiment of the present invention, a disease involving muscular disorder or myonecrosis can be detected or diagnosed by measuring the Tetranor-PGDM in a sample isolated from a subject affected or potentially affected by muscle degenerative disease. Specifically, the subject can be diagnosed with muscle degenerative disease when the concentration or content of the Tetranor-PGDM in a sample exceeds a predetermined value. The predetermined value of the Tetranor-PGDM in a sample isolated from a subject can be determined from the measured Tetranor-PGDM in samples from a healthy individual and from a muscle degenerative disease patient.

The method for determining the efficacy of therapeutic agents and/or therapeutic methods compares the measured values of Tetranor-PGDM in samples from a muscle degenerative disease patient before and after the treatment/administration of a therapeutic agent. The method determines that the treatment and the administration of the therapeutic agent are effective when the measured value of Tetranor-PGDM in the sample has lowered significantly or marginally significantly after the treatment/administration of the therapeutic agent. On the other hand, the method determines that the therapeutic agent/therapeutic method are ineffective when there is no significant or marginally significant difference in the measured values of Tetranor-PGDM in the sample before and after the treatment/administration of the therapeutic agent.

According to another aspect of the present invention, a diagnosis kit can be provided that uses antibodies for the detection of Tetranor-PGDM in a sample.

As used herein, "subject" refers to mammals, including, for example, humans, monkeys, bovines, horses, rats, mice, guinea pigs, rabbits, dogs, cats, sheep, and goats. Preferably, the subject is a human.

The Tetranor-PGDM measured by the method of the present invention is found as a metabolite of $PGD_2$ in urine.

Tetranor-PGDM also can be found in blood and feces. In the present invention, the sample isolated from a subject is preferably urine, feces, blood, blood plasma, or serum, more preferably urine.

As used herein, the term "measure" encompasses detection, quantification, and semiquantification. As such, "measuring Tetranor-PGDM" means both detecting Tetranor-PGDM in a sample, and measuring the expression level. The term also encompasses determining whether the expression level is at or above a predetermined value, in other words, detecting expression when the expression level is at or above a predetermined value.

Examples of the method that can be used to measure Tetranor-PGDM include GC-MS, HPLC, high-performance liquid chromatography-tandem mass spectrometry (HPLC-MS/MS), enzyme immunoassay (EIA), radioimmunoassay (RIA), fluorescent immunoassay (FIA), ELISA, and an enzyme method. Of these, high-performance liquid chromatography-tandem mass spectrometry (HPLC-MS/MS) is preferred, and, for ease of procedure, immunoassays using anti-Tetranor-PGDM antibodies, specifically enzyme immunoassay (EIA), radioimmunoassay (RIA), fluorescent immunoassay (FIA), and ELISA are preferred, and enzyme immunoassay (EIA) and ELISA are particularly preferred.

Examples of the muscle degenerative disease include progressive muscular dystrophy, congenital muscular dystrophy, limb-girdle muscular dystrophy, facioscapulohumeral muscular dystrophy, myotonic muscular dystrophy, amyotrophic lateral sclerosis, myopathy, muscle strain, cardiomyopathy (myocardial infarction), and diabetic peripheral vascular disease (vascular smooth muscle disorder). Muscular dystrophies and amyotrophic lateral sclerosis, such as progressive muscular dystrophy, congenital muscular dystrophy, limb-girdle muscular dystrophy, facioscapulohumeral muscular dystrophy, and myotonic muscular dystrophy, are preferred.

The therapeutic agent that can be used for the determination of therapeutic efficacy for muscle degenerative diseases is not particularly limited, and any therapeutic agent can be used, including, for example, hematopoietic prostaglandin D synthetase (HPGDS) inhibitors and prostaglandin D receptor antagonists, of which hematopoietic prostaglandin D synthetase (HPGDS) inhibitors are preferred.

It is preferable that the Tetranor-PGDM concentration in a sample be measured by immunoassay, because it easily enables simultaneous measurements of large sample numbers.

The anti-Tetranor-PGDM antibodies used for the immunoassay and the kit may be, for example, polyclonal antibodies or monoclonal antibodies.

With regard to antibody production, polyclonal antibodies and monoclonal antibodies may be produced by administering Tetranor-PGDM and immunizing an animal (rat, mouse, guinea pig, rabbit, dog, cat, sheep, goat, etc.). Alternatively, polyclonal antibodies and monoclonal antibodies may be obtained from the serum collected from an animal (rat, mouse, guinea pig, rabbit, dog, cat, sheep, goat, etc.) and treated by a known method after a predetermined time period from the interval administration of the animal with a suspension mixture of a suitable adjuvant and Tetranor-PGDM bound to a suitable protein, for example, such as bovine serum albumin (BSA), globulin, thyroglobulin, and hemocyanin.

Specifically, monoclonal antibodies can be obtained from hybridomas produced by fusing myeloma cells with monoclonal antibody-producing cells obtained from spleen after immunizing an animal with an immunogen, for which the Tetranor-PGDM used for the production of polyclonal antibodies and optionally attached to a suitable protein is used.

The hybridomas can be obtained as follows. The Tetranor-PGDM, obtained as above either alone or as a complex with a protein, is intraperitoneally, intravenously, or subcutaneously administered with a complete Freund's adjuvant to a suitable animal (such as mouse, rat, and rabbit) every 2 to 3 weeks in divided portions to immunize the animal. The antibody-producing cells originating in the spleen or other organs are then fused with tumor cells, such as myeloma cells, that can proliferate in a test tube. The cells can be fused by using polyethylene glycol according to the ordinary method of Kohler and Milstein (Nature, vol. 256, 495 (1975)), or by using Sendai virus.

The Tetranor-PGDM immunoassay is performed using the anti-Tetranor-PGDM antibodies obtained as above. Preferably, the immunoassay is performed by known competitive immunoassay methods targeting the measured substance Tetranor-PGDM. Examples of such methods include enzyme immunoassay (EIA), fluorescent immunoassay, luminescent immunoassay, and radioimmunoassay (RIA), classified according to the labeling substance. Of these, EIA is particularly preferred.

Typically, labeled antigens are used for the competition method. Examples of labeling substances include enzymes, fluorescent substances, luminescent substances, and radioisotopes. The conjugation between the labeling substance and antigens can be made using known methods that form a covalent bond or a non-covalent bond. Examples of such conjugation methods include a method that forms a covalent bond using, for example, a condensing agent, and a method that uses various crosslinkers (see, for example, *Tanpakushitsu Kakusan Kouso* (PNE), Separate Volume 31, pp. 37 to 45 (1985)). The covalent binding method can be used to produce labeled antigens by using the functional group present on the antigens, or by binding a functional group such as a thiol group, an amino group, a carboxyl group, and a hydroxyl group after introducing these groups using an ordinary method. The non-covalent binding method may be, for example, a physical adsorption method.

Preferably, Tetranor-PGDM is immunoassayed, for example, as follows. Through a competition reaction between a predetermined amount of labeled Tetranor-PGDM, anti-Tetranor-PGDM antibodies, and a sample containing Tetranor-PGDM (particularly, a urine sample), the Tetranor-PGDM in the sample is quantified from the amount of the labeled antigens that have bound to the antibodies or did not bind to the antibodies.

The labeled antigens bound to the antibodies can be isolated from the unbound labeled antigens through addition of anti-immunoglobulin antibodies and isolation of the precipitated (labeled antigen)-(anti-Tetranor-PGDM antibody)-(anti-immunoglobulin antibody) conjugates, followed by the measurement of the labeling substance that has bound to the conjugates or that did not bind to the conjugates. The method, called a double antibody technique, also can be performed using a method that uses a charcoal filter. The anti-immunoglobulin antibody assay also can be performed by measuring the anti-immunoglobulin antibodies that have bound to the solid phase, or by measuring the labeling substance that has bound to the solid phase or did not bind to the solid phase. The anti-immunoglobulin antibodies may be bound to the solid phase by using known methods, for example, such as a physical adsorption method, a chemical binding method that uses a crosslinker or a covalent bond, and a binding method that uses an avidin-biotin bond. The measurement of the labeling substance should be selected according to the type of labeling substance used.

The kit of the present invention includes anti-Tetranor-PGDM antibodies. In a more preferred embodiment, the kit includes labeled Tetranor-PGDM, and anti-Tetranor-PGDM antibodies. As required, the kit may also include, for example, anti-immunoglobulin antibodies that bind to the anti-Tetranor-PGDM antibodies, a sample diluting solution, a diluting solution for the antibodies and labeled Tetranor-PGDM, and standard Tetranor-PGDM of a known concentration. For EIA, the kit may additionally include, for example, a substrate and a stop solution.

The sample used for the measurement of Tetranor-PGDM in the present invention may be specifically, for example, urine collected from humans.

The efficacy determining method for muscle degenerative disease patients compares the measured values of Tetranor-PGDM in a sample (specifically, urine) before and after the administration of a therapeutic agent.

The sample may be a pool of urine collected for a day, or a collected sample may be directly used for the measurement. The collected urine may be preserved at room temperature, preferably at low temperature before use in the measurement.

The Tetranor-PGDM in a sample may be measured relative to the total amount of the collected sample, or relative to a part of the collected sample with consideration to correction by reference substances such as creatinine.

For ease of procedure, the Tetranor-PGDM in a sample is preferably measured relative to a part of the collected sample with consideration to correction by creatinine.

The predetermined value used in the present invention is described below.

The predetermined value used for the determination of therapeutic efficacy for muscle degenerative disease patients can be determined by measuring the Tetranor-PGDM in samples from a healthy individual and a patient, and each measured value can then be used to determine a "predetermined value" as a criteria for determining the presence or absence of therapeutic efficacy according to an ordinary method.

For example, when urine is used as a sample, the predetermined value should preferably be determined using a daily amount of urine pooled form each of a healthy individual and a muscle degenerative disease patient, or urine collected at a preset time.

In the method for determining therapeutic efficacy through the Tetranor-PGDM measurement, the concentration of the Tetranor-PGDM contained in the urine of a patient before administration of a therapeutic agent under controlled treatment is used as the predetermined value, and the therapeutic agent and/or the therapeutic method are determined as being effective when the urine Tetranor-PGDM concentration is significantly or marginally significantly lower than the predetermined value. The therapeutic method and/or the administration of the therapeutic agent are then continued. On the other hand, when there is no significant or marginally significant decrease in the Tetranor-PGDM concentration in urine, the therapeutic method and/or the therapeutic agent are determined as being ineffective, and other therapeutic agents and/or therapeutic methods are sought.

EXAMPLES

The present invention is described below in more detail based on Example. It should be noted, however, that the invention is not limited by the following Example.

Example 1

1. Materials and Methods
(1) Materials and Samples
The following animals were used as muscular dystrophy model animals.
Muscular dystrophy mouse: mdx (C57Bl/10 ScSn; available from JAX Laboratories)
Muscular dystrophy dog: $CXMD_J$ ($CXMD_J$; available from National Center of Neurology and Psychiatry)
For comparison, animals of the same lineage were used as controls.
Wild-type mouse (C57BL/10 ScSn; available from JAX Laboratories)
Normal beagle (available from National Center of Neurology and Psychiatry)
(2) Test Compounds
The following test compounds, available as known hematopoietic prostaglandin D synthetase (HPGDS) inhibitors, were used.
Test compound 1: 4-benzhydryloxy-1-{3-(1H-tetrazol-5-yl)-propyl}piperidine (Jpn. J. Pharmacol., 78, 1-10 (1998))
Test compound 2: N-methoxy-N-methyl-4-(5-benzoyl-benzimidazol-2-yl-3,5-dimethylpyrrole-2-carboxamide (WO2007007778)
(3) Collection of Mouse Urine
A solvent (0.5% methylcellulose solution) or test compound 1 was orally administered to mdx mice, 4 weeks old, for 5 days at a dose of 30 mg/kg. Using a metabolism cage for mice, urine was collected over the course of about 12 hours before the administration of test compound 1 and 5 days after the administration. For comparison, urine was also collected from wild-type mice of the same weeks old and the same lineage used as a control. The creatinine concentration in urine was measured using a measurement kit (L-type Wako CRE M, Wako Pure Chemical Industries, Ltd.).
(4) Collection of Dog Urine
$CXMD_J$ was orally administered with a solvent (0.5% methylcellulose solution) or test compound 2 for about 1 year, followed by the administration of test compound 2 for the solvent-administrated dog, and the solvent for the test compound 2-administered dog. Urine was collected before switching from the solvent to test compound 2, and from test compound 2 to the solvent. Urine was collected over time after the administered solution was switched. For comparison, urine was also collected from normal beagles used as a control.
(5) Urine Pretreatment
The urine (200 µL) collected from the mice or dogs was mixed with 5 ng of deuterium-labeled Tetranor-PGDM-d6 (Cayman Chemical) used as internal standard. The volume was adjusted to 2 mL with purified water, and pH was adjusted to 3. The urine was then injected to a Sep-Pak Vac C18 cartridge (Waters) equilibrated with acetonitrile (5 mL) and purified water (5 mL). The sample was washed with a 10% acetonitrile solution (5 mL) prepared using purified water, and with hexane (10 mL), and eluted with ethyl acetate (5 mL) before being dried under a stream of nitrogen. The residue was dissolved in a 10% acetonitrile solution (100 µL) prepared using purified water, and used as a measurement sample.
(6) Tetranor-PGDM Measurement
The pretreated urine sample was used for the measurement of Tetranor-PGDM levels. A high-performance liquid chromatography-tandem mass spectrometry (HPLC-MS/MS) apparatus was used for the measurement. The measurement used the HPLC apparatus Prominence System (system controller CBM-20A, two delivery units LC-20AD, online deaerator DGU-20A$_3$, column oven CTO-20A, autosampler SIL-20AC with cooling function, Shimadzu Corporation), the guard column InertsilODS3 (inner diameter 2.1 mm×length 50 mm; GL Science), and the separation column InertsilODS3 (inner diameter 2.1 mm×length 250 mm; GL Science). The mobile phase had a concentration gradient of 0.01% to 0.2% formic acid or 0.01% to 0.2% acetic acid, and acetonitrile or acetonitrile/methanol (90:10). The flow rate was 0.2 mL/min. The column oven was set to 37° C., and the autosampler to 4° C. A triple-quadrupole mass spectrometer (4000 Q TRAP LC/MS/MS system, Applied Biosystems) that uses electrospray ionization as the ion source was used for the MS/MS section. MRM (Multiple Reaction Monitoring) was used for quantification. In this technique, only the true parent ions are specifically selected from the mass of the parent ions (precursor ion) and of the fragment ions resulting from CID (collision-induced dissociation), and the parent ions are accurately quantified from the area of the selected ions. Specifically, the parent ions of the target molecule are produced by electrospray ionization, and these parent ions are isolated by a first mass analyzer (Q1). In a colliding section (Q2), fragment ions characteristic of the parent ions are produced by CID (collision-induced dissociation). The fragment ions are then isolated in a second mass analyzer (Q3), and detected at the detector provided downstream. Tetranor-PGDM (mass number 328) was detected by using any of the ions with a m/z (mass number charge) of 155, 143, and 109 produced by further decomposing the product ions with a m/z of 327 by CID (collision-induced dissociation). The internal standard Tetranor-PGDM-d6 (mass number 334) was detected by using any of the product ions with a m/z (mass number÷charge) of 161, 149, and 109 produced by further decomposing the product ions with a m/z of 333 by CID (collision-induced dissociation). Data analysis was performed with the software Analyst Version 1.4.1 attached to MS/MS. Area calculations were performed for the peaks originating from the Tetranor-PGDM in the resulting mass chromatogram, and each peak was quantified from the standard curve created from the standard sample. In the quantification, correction was made by using the area value of the peak originating from the Tetranor-PGDM-d6 introduced as the internal standard for the correction of the extraction efficiency and ionization efficiency in each analysis.

(7) Symptom Evaluation

For the symptom evaluation of the mdx mice, the forefoot grip strength was measured using a grip dynamometer for mice (traction meter; BrainSienceldea). Each measurement was made in 2 min, and the mean value of five trials was calculated.

2. Results (1) Tetranor-PGDM Concentration Levels are High in the Urine of mdx Mice The Tetranor-PGDM concentration after correction with the urine creatinine concentration was 17.8±0.8 ng/mg Cre (mean value±standard error, p<0.0003) in the mdx mice, a value about three times higher than the value 6.8±1.0 ng/mg Cre (mean value±standard error) obtained from the wild-type mice. This result suggests that the urine Tetranor-PGDM concentration can be used as a urine marker for the symptom development in muscular dystrophy.

(2) HPGDS Inhibitor Improves Symptoms in mdx Mice and Lowers Urine Tetranor-PGDM Concentration The effect of HPGDS inhibitor for symptoms in mdx mice was evaluated. In contrast to the solvent-administered group that showed no significant change in the forefoot grip strength, the mdx mice orally administered with test compound 1 in a repeated fashion had a significantly increased forefoot grip strength (FIG. 1, right). The Tetranor-PGDM concentration measured in the urine of the same mdx mice were significantly lower in the test compound 1-administered group (FIG. 1, left). The result suggests that there is a correlation between symptom improvement and changes in urine Tetranor-PGDM concentration in mdx mice.

(3) Tetranor-PGDM Concentration Levels are High in the Urine of CXMD$_J$

The muscular dystrophy model dog CXMD$_J$ had higher Tetranor-PGDM concentration levels in urine than normal dogs, and the Tetranor-PGDM concentration decreased in the urine of the CXMD$_J$ administered with test compound 2 (Table 1). This result suggests that the urine Tetranor-PGDM concentration can be used as a urine marker for the symptom development in muscular dystrophy.

TABLE 1

Tetranor-PGDM concentration in the urine of muscular dystrophy model dogs

|  | Tetranor-PGDM concentration (ng/ml) |
| --- | --- |
| Normal dog (1) | 5.9 |
| Normal dog (1) | 9.3 |
| Normal dog (1) | 5.0 |
| Normal dog (1) | 5.8 |
| CXMD$_J$ dog | 27.8 |
| HPGDS inhibitor-administered CXMD$_J$ dog | 17.9 |

Figure 2:
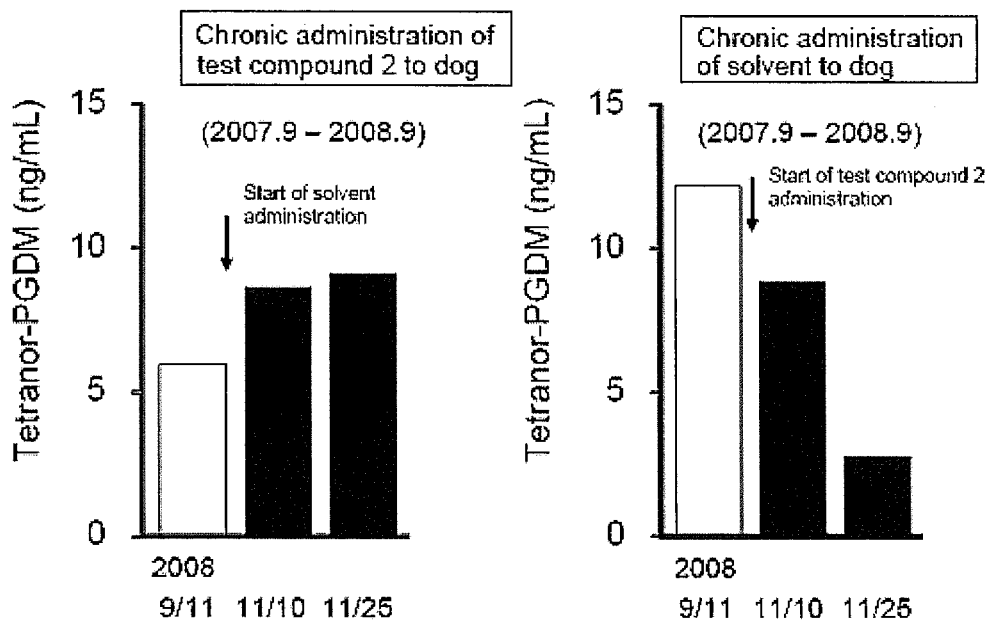
FIG. 2 is a diagram showing changes in urine Tetranor-PGDM concentration after administering a solvent following about one year of HPGDS inhibitor administration (left), and changes in Tetranor-PGDM concentration in the urine of muscular dystrophy dog (CXMDA that received the solvent for about one year before being administered with the inhibitor (right).

(4) Administration of HPGDS Inhibitor Lowers Urine Tetranor-PGDM Concentration in CXMD$_J$ The urine Tetranor-PGDM concentration increased and the symptom scores worsened in CXMD$_J$ that received the solvent after being orally administered with test compound 2 for about 1 year (FIG. 2, left). On the other hand, the urine Tetranor-PGDM concentration decreased and the symptom scores improved in CXMD$_J$ that received the inhibitor after being orally administered with the solvent for about 1 year (FIG. 2, right). These results suggest that changes in urine Tetranor-PGDM concentration can be used as a marker for determining or predicting the effect of therapeutic agent administration in muscular dystrophy.

The invention claimed is:

1. A method for detecting a muscle degenerative disease using a urine sample, comprising
    obtaining a urine sample from a subject suspected of suffering from a muscle degenerative disease;
    measuring Tetranor-PGDM content in said urine sample; and
    comparing the concentration of said Tetranor-PGDM with the concentration of Tetranor-PGDM in urine from normal subjects, wherein a high concentration of Tetranor-PGDM in said urine sample indicates the possible presence of a muscle degenerative disease.

2. The method according to claim 1, wherein the Tetranor-PGDM is measured by using high-performance liquid chromatography-tandem mass spectrometry (HPLC-MS/MS), enzyme immunoassay (EIA), radioimmunoassay (RIA), fluorescent immunoassay (FIA), ELISA, or an enzymatic method.

3. The method according to claim 1, wherein the muscle degenerative disease is progressive muscular dystrophy, congenital muscular dystrophy, limb-girdle muscular dystrophy, facioscapulohumeral muscular dystrophy, myotonic muscular dystrophy, amyotrophic lateral sclerosis, or myopathy.

4. A method for determining the efficacy of a therapeutic agent and/or a therapeutic method for a muscle degenerative disease, comprising
- obtaining a first urine sample from a subject prior to undergoing therapy for a muscle degenerative disease;
- measuring Tetranor-PGDM concentration in said first urine sample;
- obtaining a second urine sample from a subject while undergoing therapy for a muscle degenerative disease;
- measuring Tetranor-PGDM concentration in said second urine sample; and
- comparing said Tetranor-PGDM concentration in said first and second urine samples, wherein a lower Tetranor-PGDM concentration in said second urine sample indicates that the therapy is efficacious.

* * * * *